United States Patent
Xam-Mar Mangrane

(10) Patent No.: US 10,130,447 B2
(45) Date of Patent: Nov. 20, 2018

(54) INTERFACE ELEMENT FOR DENTAL PROSTHESES

(71) Applicant: Esteban Xam-Mar Mangrane, Lleida (ES)

(72) Inventor: Esteban Xam-Mar Mangrane, Lleida (ES)

( * ) Notice: Subject to any disclaimer, the term of this patent is extended or adjusted under 35 U.S.C. 154(b) by 0 days.

(21) Appl. No.: 14/914,143

(22) PCT Filed: Sep. 23, 2013

(86) PCT No.: PCT/ES2013/070661
§ 371 (c)(1),
(2) Date: Feb. 24, 2016

(87) PCT Pub. No.: WO2015/040250
PCT Pub. Date: Mar. 26, 2015

(65) Prior Publication Data
US 2016/0213450 A1    Jul. 28, 2016

(51) Int. Cl.
*A61C 8/00* (2006.01)
*A61C 13/00* (2006.01)
*A61C 13/225* (2006.01)

(52) U.S. Cl.
CPC .......... *A61C 8/0054* (2013.01); *A61C 8/0048* (2013.01); *A61C 8/0053* (2013.01); *A61C 8/0068* (2013.01); *A61C 8/0069* (2013.01); *A61C 8/0074* (2013.01); *A61C 13/0004* (2013.01); *A61C 13/225* (2013.01)

(58) Field of Classification Search
CPC ... A61C 8/0054; A61C 8/0048; A61C 8/0053; A61C 8/0068; A61C 8/0069; A61C 8/0074; A61C 8/005; A61C 13/225; A61C 13/0004

USPC .......... 433/172, 173, 174, 181, 182, 41, 43
See application file for complete search history.

(56) References Cited

U.S. PATENT DOCUMENTS 4,758,161 A * 7/1988 Niznick ............... A61C 8/0001
433/173
5,116,225 A   5/1992 Riera
(Continued)

FOREIGN PATENT DOCUMENTS

CA   2920441 A1   3/2015
EP   0506636 A2   9/1992
(Continued)

OTHER PUBLICATIONS

International Search Report of PCT/ES2013/070661 dated Jun. 23, 2014.

*Primary Examiner* — Heidi M Eide
(74) *Attorney, Agent, or Firm* — Sughrue Mion, PLLC

(57) ABSTRACT

An interface element for dental prostheses, having a hollow cylindrical body with two different sections, one lower section (a) of greater outer diameter and another upper section (b) of smaller outer diameter, each provided externally with retention circular grooves (2). The element had an internal seat (4) for a screw head (5) which fixes the implant, and a lower base (6). A side mortise (7) is provided that covers the upper section (b) and provides a side opening for the inclined entrance of the screw (5) and screwdriver (8). The element further includes two flat surfaces (9) at diametrically opposite sides of the lower section.

18 Claims, 8 Drawing Sheets

(56) References Cited

U.S. PATENT DOCUMENTS

| | | | | |
|---|---|---|---|---|
| 5,427,906 A | * | 6/1995 | Hansen | A61C 8/0048 |
| | | | | 433/173 |
| 5,782,918 A | * | 7/1998 | Klardie | A61C 8/005 |
| | | | | 433/172 |
| 5,873,721 A | | 2/1999 | Willoughby | |
| D413,383 S | * | 8/1999 | Vryonis | D24/156 |
| 5,947,733 A | | 9/1999 | Sutter et al. | |
| 6,126,445 A | | 10/2000 | Willoughby | |
| 6,142,782 A | * | 11/2000 | Lazarof | A61C 8/0001 |
| | | | | 433/174 |
| 6,159,010 A | | 12/2000 | Rogers et al. | |
| 6,848,908 B2 | * | 2/2005 | Bjorn | A61C 8/005 |
| | | | | 433/172 |
| 7,338,286 B2 | * | 3/2008 | Porter | A61C 8/0001 |
| | | | | 433/172 |
| 8,425,231 B1 | * | 4/2013 | Hochman | A61C 8/008 |
| | | | | 433/173 |
| 8,597,023 B2 | * | 12/2013 | Zipprich | A61C 8/005 |
| | | | | 433/173 |
| 9,522,051 B2 | | 12/2016 | Engman | |
| 2001/0055743 A1 | * | 12/2001 | Yeung | A61C 8/005 |
| | | | | 433/173 |
| 2005/0214714 A1 | * | 9/2005 | Wohrle | A61C 8/0018 |
| | | | | 433/173 |
| 2007/0154864 A1 | | 7/2007 | Deer et al. | |
| 2008/0153066 A1 | * | 6/2008 | Schlussel | A61C 8/005 |
| | | | | 433/213 |
| 2009/0117520 A1 | | 5/2009 | Kikuchi | |
| 2009/0202962 A1 | | 8/2009 | Xam-Mar Mangrane | |
| 2010/0304334 A1 | * | 12/2010 | Layton | A61C 8/005 |
| | | | | 433/173 |
| 2011/0262883 A1 | * | 10/2011 | Hung | A61C 8/0001 |
| | | | | 433/174 |
| 2012/0322030 A1 | * | 12/2012 | Fromovich | A61C 8/005 |
| | | | | 433/173 |
| 2013/0004915 A1 | * | 1/2013 | Bellanca | A61C 8/0018 |
| | | | | 433/173 |
| 2013/0209958 A1 | | 8/2013 | Benz et al. | |

FOREIGN PATENT DOCUMENTS

| | | | | |
|---|---|---|---|---|
| EP | 1419746 A2 | | 5/2004 | |
| EP | 2514390 A1 | | 10/2012 | |
| ES | 1072599 U | | 8/2010 | |
| GB | 2495513 A | * | 4/2013 | A61C 8/0068 |
| MX | JL04000042 A | | 5/2006 | |
| WO | WO 98/55040 | * | 5/1998 | A61C 8/00 |
| WO | 2008157137 A1 | | 12/2008 | |
| WO | 2012045356 A1 | | 4/2012 | |
| WO | 2013/004386 A1 | | 1/2013 | |
| WO | 2013004387 A1 | | 1/2013 | |
| WO | WO 2013004386 A1 | * | 1/2013 | A61C 8/0001 |
| WO | 2014064558 A2 | | 5/2014 | |
| WO | 2014173539 A1 | | 10/2014 | |
| WO | 2014200404 A1 | | 12/2014 | |
| WO | 2015040250 A1 | | 3/2015 | |

* cited by examiner

INTERFACE ELEMENT FOR DENTAL PROSTHESES

CROSS REFERENCE TO RELATED APPLICATIONS

This application is a National Stage of International Application No. PCT/ES2013/070661 filed Sep. 23, 2013, the contents of all of which are incorporated herein by reference in their entirety.

OBJECT OF THE INVENTION

The invention, an interface element for dental prostheses, which relates to a metal part known in the dentistry-implantology industry as interface or titanium base, is used as a connection element between a dental prosthesis structure and the screw that allows fixing said prosthesis on an implant, and said element has the special feature of having an innovative structural configuration that improves its functionality and, particularly, it is designed to vary the inclination of insertion of the screw to correct possible problems of incorrect angular positioning of the implant.

The field of application of the present invention belongs to the dental-implantology industry, focusing specifically on the field of dental implants, particularly on structures, usually made with CAD/CAM systems, which are screwed onto dental implants with passive fit. The dental CAD/CAM (CAD computer-aided design, computer aided design and CAM computer-aided manufacturing, computer aided manufacturing) system allows manufacture of dental prostheses designed and manufactured by computer.

BACKGROUND OF THE INVENTION

At present there are different systems and solutions for achieving a functional dental prosthesis. One is them is the use of biocompatible metallic elements located between the implant and the dental prosthesis, known as interfaces.

Interfaces are parts generally made out of titanium in the form of a stump screwed onto the implant (part not visible that is inserted into the jaw bone) and on which the dental structure (outer visible part that imitates the dental part or parts) is cemented with a specific dual cement permanently. Another alternative is that said interfaces are welded onto the structure, which depends on the design of the prosthesis and the materials used.

The use of the interface is intended to obtain a passive fit of the structure on the implants, since the structure is cemented or welded onto the interfaces at the end of the prosthesis manufacturing process, obtaining a stress-free structure.

The interfaces also protect the mechanical operation of the screwing of the structure on the implants, because the screw sits and presses on titanium. Another objective is to protect the connection of the implant. When zirconium structures are directly screwed onto the implant, they may impair the connection of the implant as the zirconium is hard and abrasive, and therefore the structures are cemented onto titanium interfaces so that the contact is titanium-titanium.

Equally, titanium structures and of other metals are cemented or welded onto the interfaces, to save time the milling time of the CAD CAM systems.

Thus, there are two main ways of putting a dental prosthesis onto implants, the first would be tightening the structure directly onto the implant and the second screwing through the structure elements used as an interface between the implant and the structure or prosthesis.

In current designs, interfaces can be found with truncated tapered body or straight body in one or two heights, and with retention areas and position as well as with the outer sanded body, internally with straight or tapered seat for the screw, and with a base with connection according to the type of implant, with the configuration of said base varying according to the type of connection of the implant, internal/external and/or anti-rotating/rotating, to achieve proper final positioning.

The anti-rotating and rotating systems of the base, consider different positioning methods, usually with a flat area for referencing and guaranteeing the position of the prosthetic structure in the implant.

International application with publication number WO2012045356A1, relates to an angled abutment for a dental-prosthetic arrangement, in which the abutment is divided into a first sub-component and a second sub-component, wherein the first sub-component can be fixed by means of a fixing screw to an implant and has a tool opening through which a tool is able to engage to reach the screw head of the fixing screw. After the first sub-component has been fixed to an implant, the second sub-component can be connected to the first sub-component, preferably via a screwed connection, and at the same time completely covers the tool opening of the first sub-component. A retaining structure facing away from the first sub-component is formed on the second sub-component and interacts with a counter-retaining structure on a prosthesis to provide a releasable connection, which can be produced without tools, between the abutment and the prosthesis.

However, the main drawback of the current interface technique is that it does not allow correcting problems of incorrect positioning of the implant, which creates an aesthetic problem that will have to be solved, for example, cementing the prosthesis screwed to a primary screwed structure.

The main objective of the present invention is, therefore, to develop a new type of interface that allows correcting the angularly incorrect position of the implants and thus achieve corrections of angles up to 30°, solving the aesthetic problem of the screw coming out in a problematical area.

It should also be noted that, as a reference to the current state of the art, at least by the applicant, the existence of any other interface with similar technical, structural and constitutive features to those presented by the interface element for dental prostheses advocated here, as claimed, is unknown.

Explanation of the Invention

Thus, the interface element for dental prostheses which the present invention proposes, refers to an interface element that allows placing screwed structures made, generally with CAD CAM systems for dental prostheses, on dental implants with a passive fix, which is specially designed to correct the possible angularly incorrect position of the implants by allowing angled insertion of up to 30° of the screw that is screwed on the implant, and also the corresponding inclined insertion of the screwdriver used to tighten said screw onto the implant.

To this end, said interface is configured from a hollow cylindrical body comprising two different heights or sections with a different outer diameter, both provided with outer retentions determined by some circular grooves machined on them for better fixing of them on the structure of the prosthesis, with the special feature of presenting a side mortise which covers the upper or distal section with a smaller diameter than the aforementioned two different sections the cylindrical body has; mortise that determines a side opening at the end of said cylindrical body of the interface element and which is the key area thereof to achieve the pursued angulation described above, since it is designed to facilitate the inclined entrance and fixing of the screw and the inclined entrance of the screwdriver up to an angle of 30°, with regard to the axial shaft of the cylindrical body that forms the interface, besides allowing freedom of lateral movement of the screwdriver of up to 90°.

It should be noted that the total height of the interface element will depend on the implant placed and this height will mark the start of change in inclination of the entrance hole made in the structure, which can reach, as indicated, up to 30°.

Said cylindrical body has, also in the conventional manner, has a base which determines a lower lip that protrudes perimetrically with respect to retention sections described above and whose height will be between 0.05 mm and 10 mm. Depending on the area of the mouth where the implant is located, it will be necessary to use an interface with more or less height on said lip.

Internally the interface piece has a seat for fixing the screw, the configuration of which will depend on the geometry of the head of said screw, which may have a straight or tapered seat, adjusted to achieve a correct fixing.

Meanwhile, the lower geometry of the base of the interface will also depend on the type of implant and will be adapted to the connection shape of said implant.

Thus, depending on the type of use of the interface we can find two types of interface with different lower geometry on their base:
- With anti-rotating base: where the connection shape of the implant is reproduced, for example hexagonal, thus achieving the non-rotation of the system. This type of geometry is generally used in unitary implants, i.e., which comprise a single dental part.
- With rotating base: where the connection shape of the implant is not reproduced, but rather only reproducing the perimeter of the connection, being circular, for example. It is used for structures of multiple tooth prosthesis or bridges and its own shape allows an optimum fit of the prosthesis.

In any case, the interface element has an innovative shape with two flat areas made at diametrically opposite points of the outer area of the lower section or with a larger diameter of the circular body that constitutes the interface element, and whose purpose is to serve as a positioning reference and to achieve better retention of the structure on the interface.

The manufacturing material of the interfaces is biocompatible metal which may be Tilite, gold alloys, alloys of chromium/cobalt, Titanium Grade 5 with or without coating of titanium nitride (TIN) or of any dental alloy.

The major improvement provided by the innovative structural design of the interface of the invention is that it allows correcting the incorrect positioning of the implant in the patient, as the screwdriver and the screw, which logically will have an appropriate design to be able to act in angulation.

With two flat areas the interface element has, especially when its base has a lower geometry with an anti-rotating system, a correct positioning of the structure on the interface is achieved which allows achieving a greater retention.

Another advantage of the interface of the present invention is that it allows flexibility when working, since it can be also used when there is no need to correct any angulation.

DESCRIPTION OF THE DRAWINGS

To complement the description being made and in order to facilitate understanding of the features of the invention, some figures are attached to this descriptive report in which the following has been represented, with an illustrative and non-limiting character.

PREFERRED MODE FOR CARRYING OUT THE INVENTION

Figure 1:
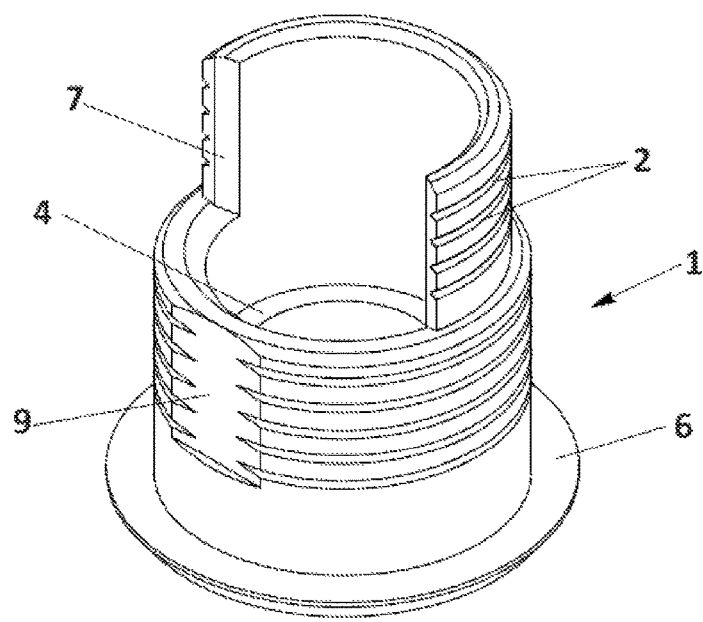
FIG. 1 shows a perspective view of an embodiment of the interface element for dental prostheses of the invention, which shows in it the outer general configuration and main parts that comprise it.
Figure 2:
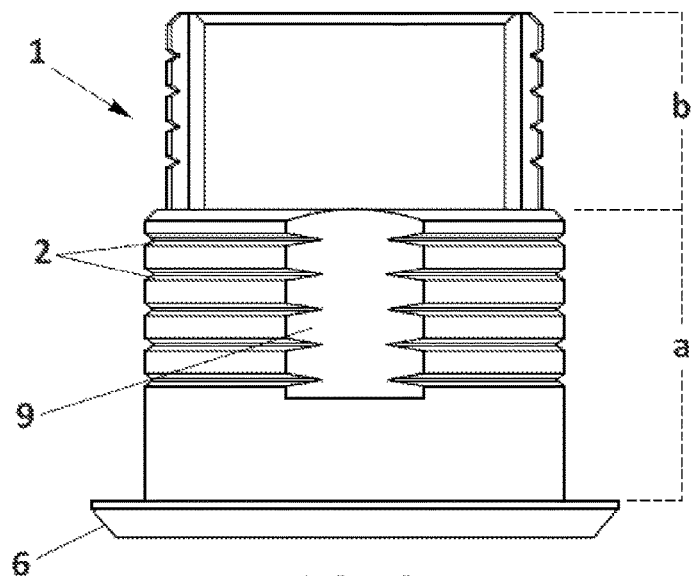
FIG. 2 shows a front elevation view of the example of interface element for dental prostheses, according to the invention, shown in FIG. 1.
Figure 3:
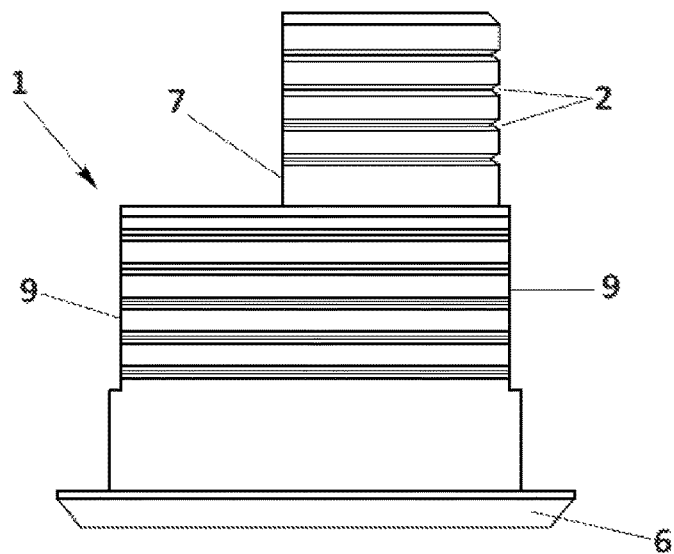
FIG. 3 shows a side elevation view of the example of interface element for dental prostheses, according to the invention, shown in FIG. 1.
Figure 4:
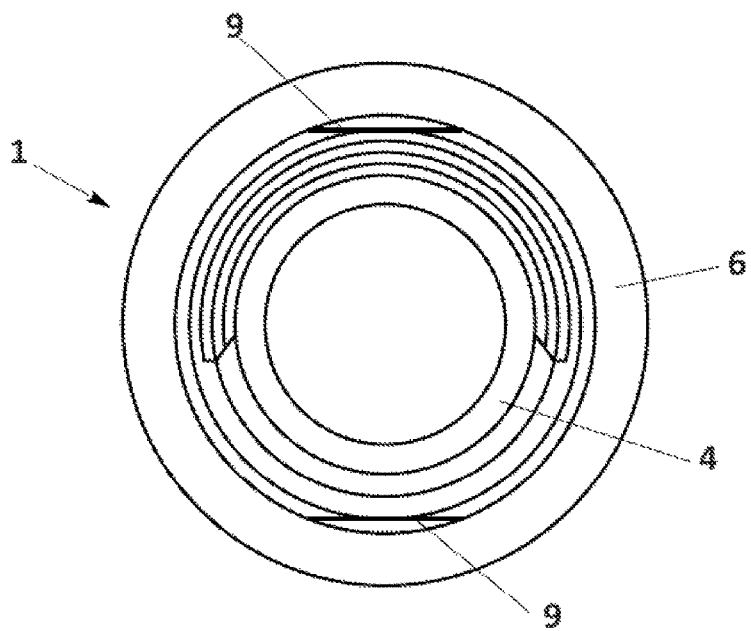
FIG. 4 shows a top plan view of the example of interface element for dental prostheses, according to the invention, shown in FIG. 1.

In view of the mentioned figures and according to the adopted numbering, we can observe therein an example of a preferred mode for carrying out the invention. The interface element (1) in question is configured from a hollow cylindrical body comprising two separate sections, one lower (a) of greater outer diameter and an upper (b) of smaller outer diameter, clearly perceptible in FIG. 2 and both equipped externally with circular retention grooves (2) to ensure better grip thereto of the structure of the prosthesis (3) it is designed for.

Figure 13:
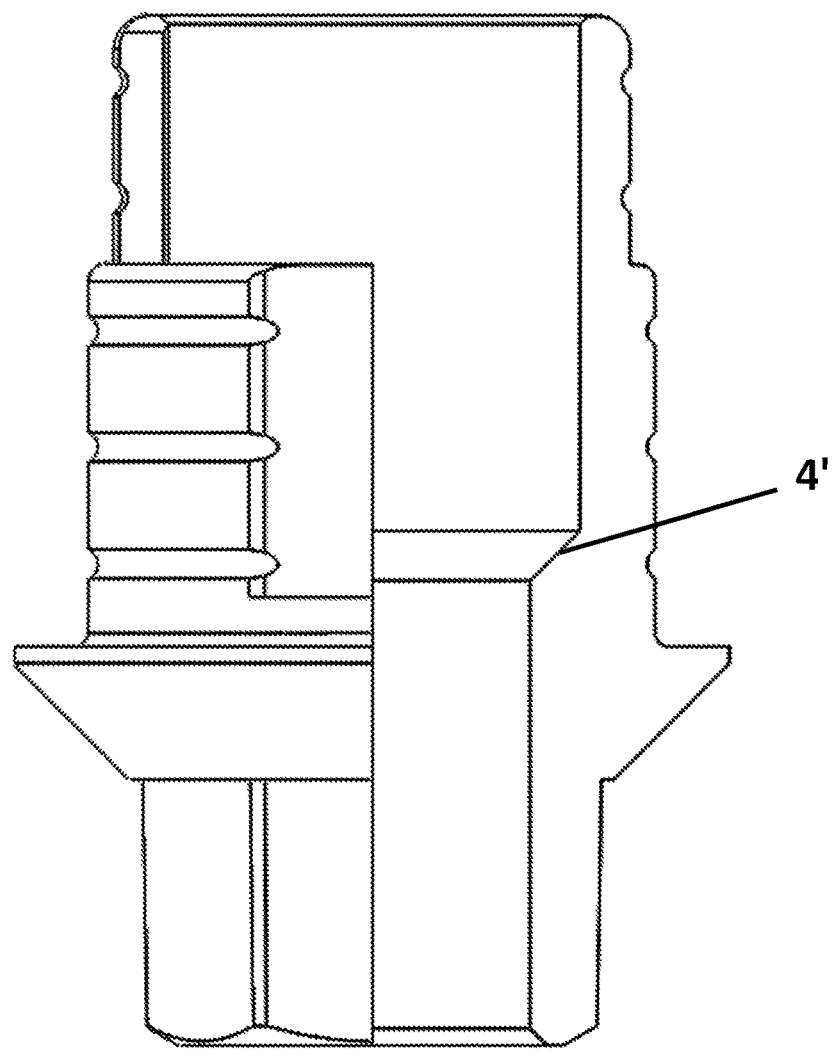
FIG. 13 shows an embodiment wherein the seat for the screw head is tapered.

Furthermore, also in an already known manner, this body has inside a seat (4), which may be straight or tapered (as shown in FIG. 13, 4'), for fixing the screw head (5) inserted through it to fix the prosthesis (3) to the implant (not shown), and with a lower base (6) which determines a perimeter lip with a height of between 0.05 mm and 10 mm.

Figure 5:
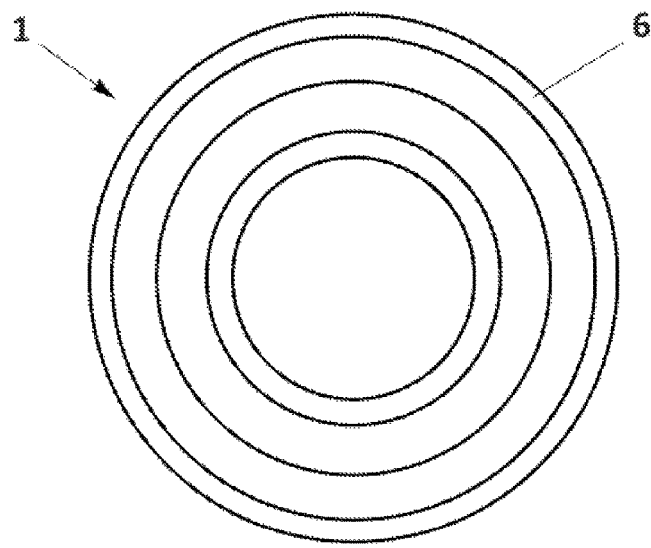
FIG. 5 shows a bottom plan view of the interface element for dental prostheses, according to the invention, in an embodiment thereof designed with a rotating geometry base.
Figure 6:
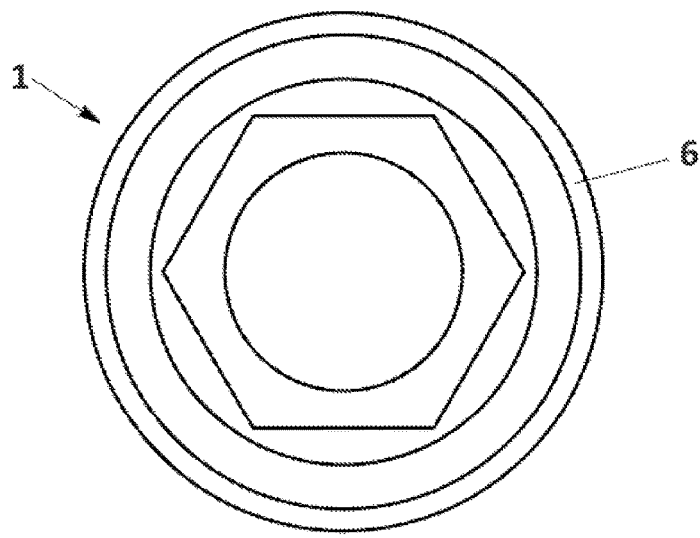
FIG. 6 shows a bottom plan view of the interface element for dental prostheses, according to the invention, in an embodiment thereof designed with an anti-rotating geometry base.
Figure 7:
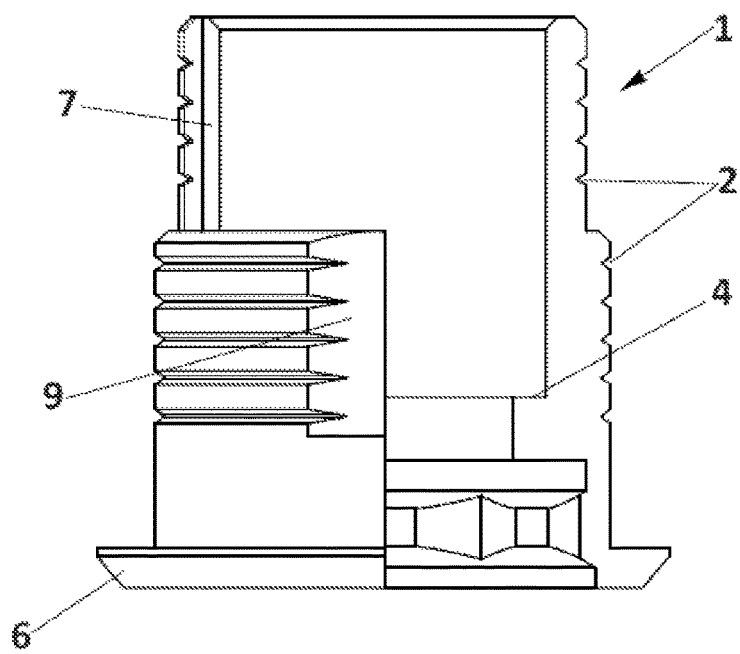
FIG. 7 shows a front elevation and partially sectional view of the example of interface element for dental prostheses according to the invention, shown in FIG. 6.
Figure 8:
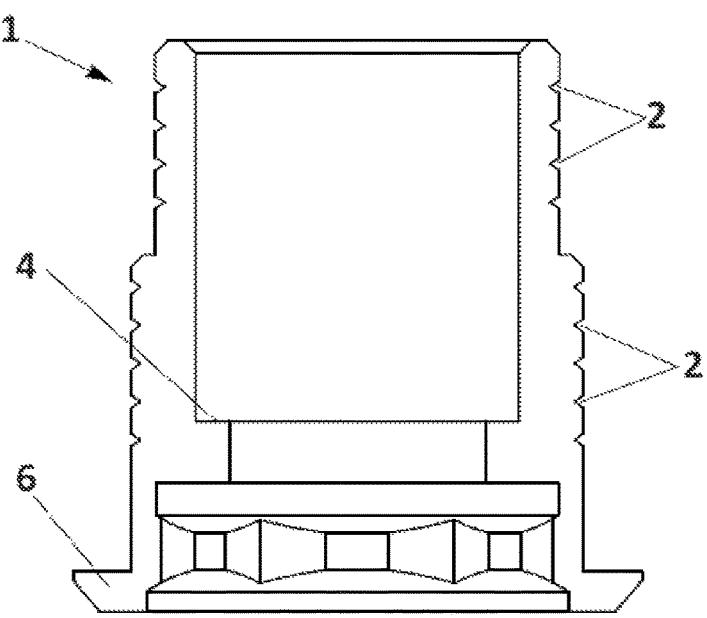
FIG. 8 is a sectional elevation view of the example of interface element for dental prostheses, according to the invention, shown in FIG. 6.
Figure 9:
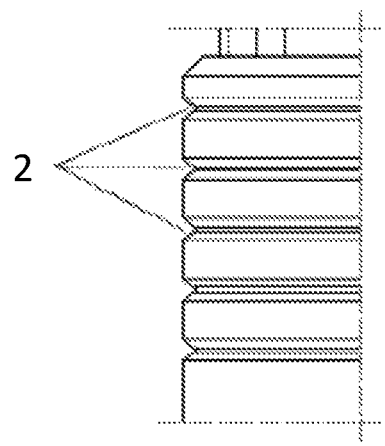
FIG. 9 shows a detailed view of the retentions externally presented by the interface element.

The geometry of said base (6), on the lower face of the interface (1) also varies depending on the type of connection the implant to which it is attached has, which may be either anti-rotating, as in the example of FIG. 6, which reproduces the form of connection of the implant to prevent rotation of the system, or rotating, as in the example of FIG. 5, where only the perimeter of the connection is reproduced, which is normally circular.

Figure 10:
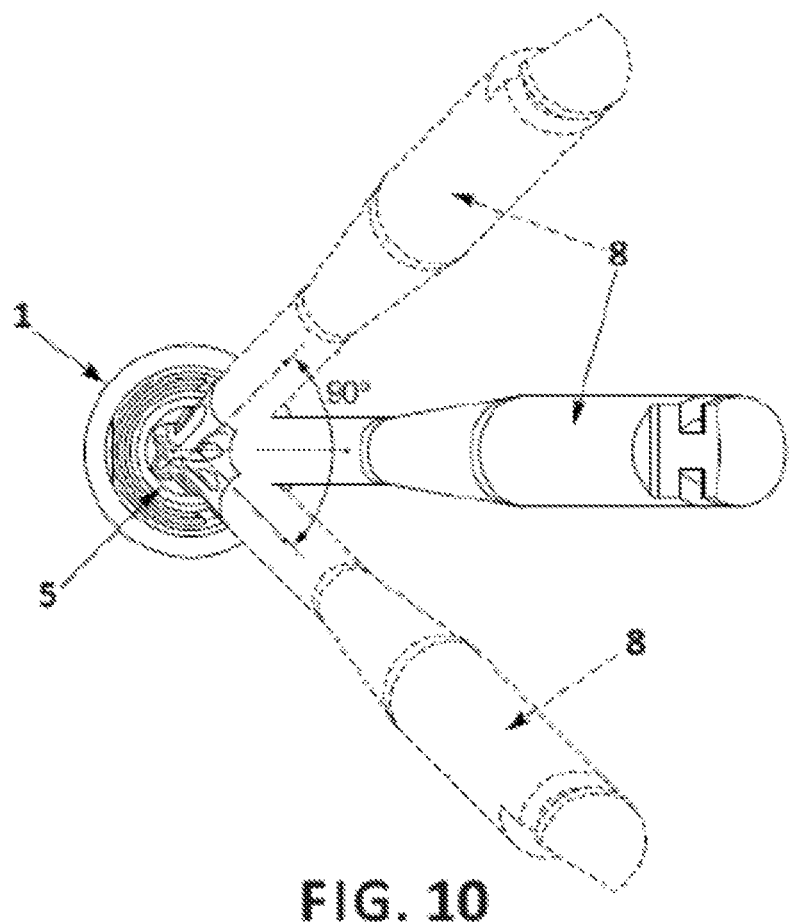
FIG. 10 shows a top perspective view of an interface element, according to the invention, with the screwdriver incorporated, showing the 90° of freedom of movement it presents.
Figure 11:
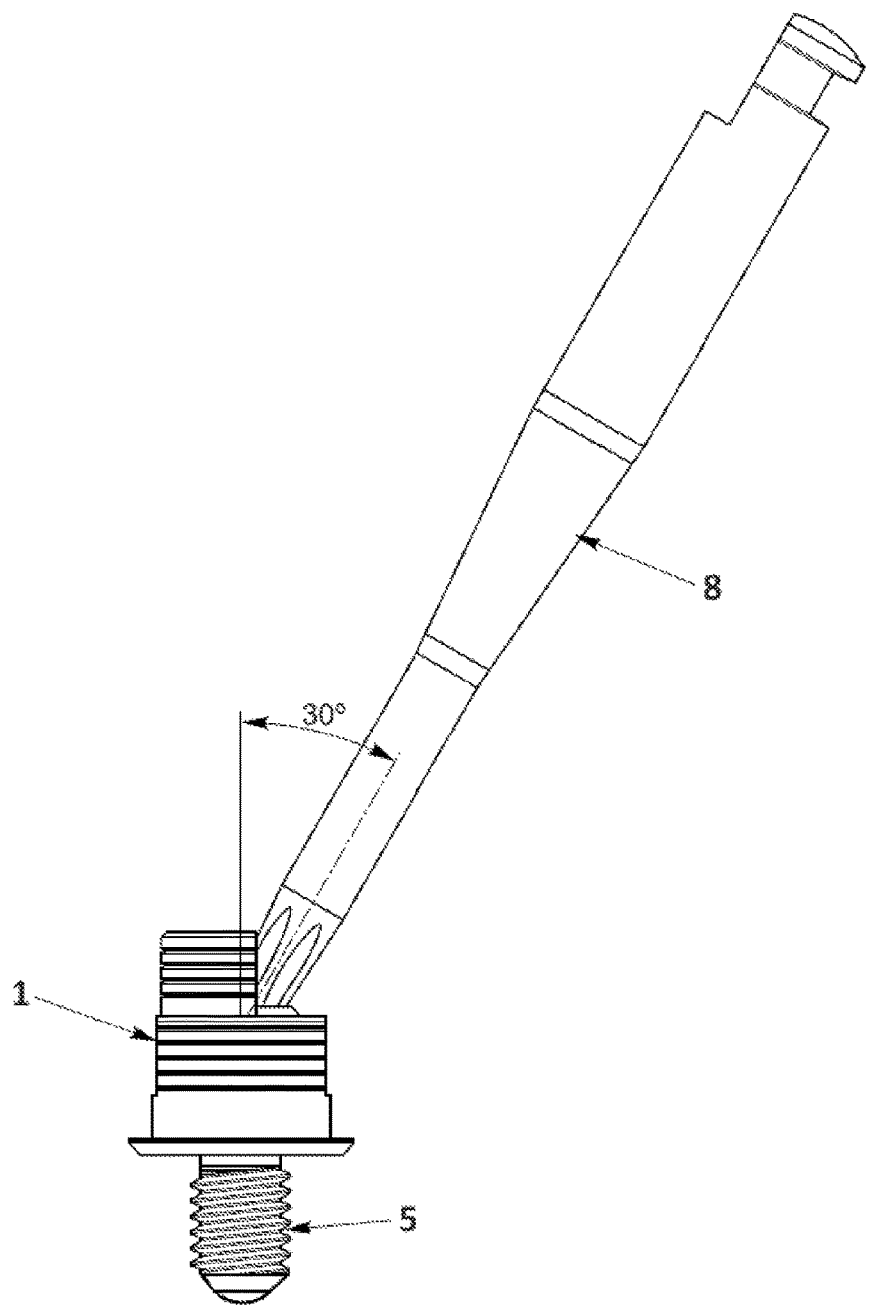
FIG. 11 shows a side elevation view of an interface element, according to the invention, with the screw and screwdriver incorporated, showing the 30° of freedom of movement said screwdriver has for fixing the screw.
Figure 12:
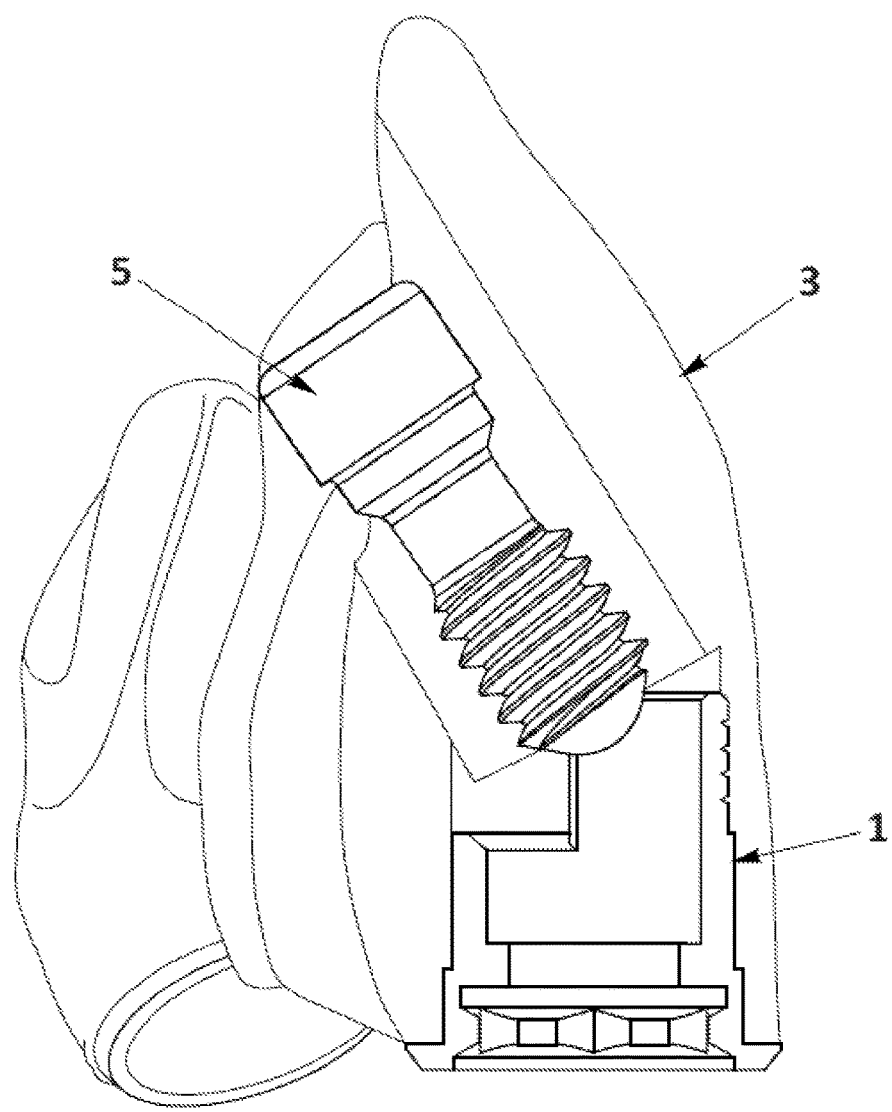
FIG. 12 shows a sectional view of the interface element with the prosthesis structure incorporated therein and showing the form of angled insertion of the screw that allows the fixing of the assembly to the implant.

From these already known features, the interface element (1) advocated has the special feature of having a side mortise (7) which covers the upper section (b) and with a smaller diameter of the above two sections (a and b) the cylindrical body of the element has, which being mortised (7) determines a side opening at the end of said cylindrical body the height of which is suitable for the entrance and inclined fixing of the screw (5) as well as for the inclined entrance of the screwdriver (8) by up to an angle of 30°, with respect to the axial shaft of the cylindrical body which forms the interface (1), as shown in FIGS. 10, 11 and 12, also allowing, thanks to the width of said side opening, a freedom of lateral movement of the screwdriver (8) of up to 90°, as shown in FIG. 10.

Additionally, the interface element (1) has two flat areas (9) formed at diametrically opposite points on the outer surface of the lower section (a) of greater diameter of the circular body intended to be a positioning reference and to achieve a better retention of the structure of the prosthesis (3) on the interface (1).

The invention claimed is:

1. An interface element for dental prostheses, configured from a hollow cylindrical body comprising:
   an internal seat (4) for a screw head (5) of a screw configured to be inserted inside the interface element so as to fix the interface element to an implant by screwing;
   a lower base (6) having a perimeter lip;
   wherein the hollow cylindrical body comprises a cylindrical wall that is incomplete due to a mortise (7), the mortise defining a side opening in the cylindrical wall configured to allow a variable inclined entrance of the screw (5) and a screwdriver (8) for threading said screw (5); and
   wherein the interface element further comprises two flat outer surfaces formed at diametrically opposed sides of a lower section of the circular body to provide a positioning reference and better retention of the prosthesis on the interface.

2. The element, according to claim 1, wherein the side opening has a height sufficient to allow the variable inclined entrance of both the screw (5) and the screwdriver (8) with an inclination from an angle of 0° up to an angle of 30°, with respect to a central axis of the cylindrical body.

3. The element, according to claim 2, wherein the side opening has a width of up to 180° and allows the freedom of lateral movement of the screwdriver (8) of up to 90°.

4. The element, according to claim 1, wherein the side opening has a width of up to 180° and allows freedom of lateral movement of the screwdriver (8) of up to 90°.

5. The element according to claim 1, wherein the seat (4) for the screw head is straight or tapered.

6. The element, according to claim 1, wherein the hollow cylindrical body comprises two separate sections that are the lower section of greater outer diameter and an upper section of smaller outer diameter such that the greater outer diameter is larger than the smaller outer diameter; and wherein the mortise is formed in the upper section.

7. The element, according to claim 6, wherein the lower section and the upper section are co-axially aligned.

8. The element, according to claim 6, wherein an interior surface of the lower section and an interior surface of the upper section revolve about a common central axis.

9. The element, according to claim 8, wherein the interior surface of the lower section defines a cylindrical surface and the interior surface of the upper section defines an incomplete cylindrical surface made incomplete by the side opening, and wherein the cylindrical surface defined by the lower section and the incomplete cylindrical surface defined by the upper section are co-axial and revolve about the common central axis.

10. The element, according to claim 9, wherein the cylindrical surface defined by the lower section and the incomplete cylindrical surface defined by the upper section are coextensive at a same constant radius from the common central axis.

11. The element, according to claim 8, wherein the interior surface of the upper section is smooth, free of threads and grooves.

12. A dental prostheses system, comprising:
    the element, according to claim 1;
    the screw for securing the cylindrical body to the implant; and
    the screw driver configured to engage and turn the screw; and
    wherein the side opening has a height sufficient to allow an inclined entrance of both the screw and the screwdriver cooperatively engaging the screw with an inclination from an angle of 0° to up to an angle of 30° with respect to a central axis of the cylindrical body.

13. An interface element for dental prostheses, configured from a hollow cylindrical body comprising:
    an internal seat for a screw head of a screw configured to be inserted inside the interface element so as to fix to an implant; and
    a perimeter outwardly extending lip at a lower end of the cylindrical body;
    wherein an upper portion of the cylindrical body is in the form of an incomplete cylindrical structure about a cylindrical axis defined by an internal cylindrical wall of less than 360 degrees that extends parallel to the cylindrical axis until terminating at a distal open free end opposite to the lower end; and
    wherein the interface element further comprises two flat outer surfaces formed at diametrically opposed sides of a lower section of the circular body to provide a positioning reference and better retention of the prosthesis on the interface.

14. The interface element for dental prostheses according to claim 13, wherein the lower section has a first diameter and the upper portion has a second diameter that is smaller than the first diameter.

15. The interface element for dental prostheses according to claim 14, further comprising circular retention grooves on each of the lower section and the upper portion for fixing the prosthesis.

16. The interface element for dental prostheses according to claim 14, wherein the incomplete cylindrical structure is defined by a cylindrical wall of no more than 180 degrees and that terminates at the distal open free end which is opposite to the lower end.

17. The interface element for dental prostheses according to claim 13, further comprising a dental prostheses cemented to the interface element.

18. An interface element for dental prostheses, configured from a hollow cylindrical body comprising:
- an internal seat for a screw head of a screw configured to be inserted inside the interface element so as to fix to an implant; and
- a perimeter outwardly extending lip at a lower end of the cylindrical body;
- wherein an upper portion of the cylindrical body is in the form of an incomplete cylindrical structure about a cylindrical axis defined by an internal cylindrical wall of less than 360 degrees that extends parallel to the cylindrical axis until terminating at a distal open free end opposite to the lower end;
- wherein a lower section has a first diameter and the upper portion has a second diameter that is smaller than the first diameter; and
- wherein the interface element further comprises circular retention grooves on each of the lower section and the upper portion for fixing the prosthesis.

* * * * *